United States Patent
Muraviev

(10) Patent No.: US 9,212,990 B1
(45) Date of Patent: Dec. 15, 2015

(54) SYSTEM AND METHODS FOR MOLECULAR DETECTION USING INTRACAVITY LASER ABSORPTION SPECTROSCOPY

(71) Applicant: Zybertec LLC, Melbourne, FL (US)

(72) Inventor: Andrey Muraviev, Orlando, FL (US)

(73) Assignee: Zybertec LLC, Melbourne, FL (US)

( * ) Notice: Subject to any disclaimer, the term of this patent is extended or adjusted under 35 U.S.C. 154(b) by 193 days.

(21) Appl. No.: 13/707,300

(22) Filed: Dec. 6, 2012

Related U.S. Application Data

(60) Provisional application No. 61/630,157, filed on Dec. 6, 2011, provisional application No. 61/711,979, filed on Oct. 10, 2012.

(51) Int. Cl.
G01N 21/39 (2006.01)
G01N 21/3504 (2014.01)
G01J 3/02 (2006.01)

(52) U.S. Cl.
CPC ............... *G01N 21/39* (2013.01); *G01J 3/0205* (2013.01); *G01N 21/3504* (2013.01); *G01N 2201/022* (2013.01); *G01N 2201/0636* (2013.01); *G01N 2201/06113* (2013.01)

(58) Field of Classification Search
CPC .... G01N 21/3504; G01N 21/39; G01J 3/0205
USPC ........................................................ 250/343
See application file for complete search history.

(56) References Cited

U.S. PATENT DOCUMENTS

| | | | |
|---|---|---|---|
| 5,432,610 A | 7/1995 | King et al. | |
| 5,437,840 A | 8/1995 | King et al. | |
| 5,650,856 A | 7/1997 | Morse | |
| 5,689,334 A | 11/1997 | Atkinson et al. | |
| 5,723,864 A | 3/1998 | Atkinson et al. | |
| 5,742,054 A | 4/1998 | Atkinson | |
| 5,841,533 A | 11/1998 | Atkinson | |
| 5,903,358 A | 5/1999 | Zare et al. | |
| 5,986,768 A | 11/1999 | Pipino | |
| 6,028,310 A | 2/2000 | Atkinson et al. | |
| 6,067,167 A | 5/2000 | Atkinson et al. | |

(Continued)

OTHER PUBLICATIONS

Zeninari, Laboratory Spectroscopic Calibration of Infrared Tunable Laser Spectrometers for the In Situ Sensing of the Earth and Martian Atmospheres, Applied Physics B: Lasers and Optics, 2006, vol. 85 p. 265-272, France.

(Continued)

*Primary Examiner* — David Porta
*Assistant Examiner* — Mindy Vu
(74) *Attorney, Agent, or Firm* — Thomas E. Toner; Shumaker, Loop & Kendrick, LLP

(57) ABSTRACT

In a gas phase analyte testing method a laser beam is generated using a laser beam from a laser gain medium located within an external laser cavity. A gain parameter of the laser gain medium is changed so that the laser gain medium emits across a range of wavelengths in response to the change. The beam is passed through a test sample as the gain parameter is changed, the test sample being positioned inside the external laser cavity. A change in the spatial or spectral mode distribution or dynamics of the laser emission spectrum is detected. It is then determined whether the change in the spatial or spectral mode distribution or dynamics of the laser emission spectrum is caused by the test sample.

14 Claims, 9 Drawing Sheets
(6 of 9 Drawing Sheet(s) Filed in Color)

(56) References Cited

U.S. PATENT DOCUMENTS

| | | | |
|---|---|---|---|
| 6,151,128 | A | 11/2000 | Huber |
| 6,363,772 | B1 | 4/2002 | Berry |
| 6,714,565 | B1 | 3/2004 | Tucker et al. |
| 6,930,822 | B2 | 8/2005 | Boggy et al. |
| 7,230,960 | B2 | 6/2007 | Nguyen et al. |
| 7,295,582 | B2 | 11/2007 | McDonald et al. |
| 7,541,586 | B2 | 6/2009 | Miller |
| 7,555,024 | B2 | 6/2009 | Ishaaya et al. |
| 7,822,081 | B2 | 10/2010 | Vilhelmsson |
| 7,826,503 | B2 | 11/2010 | Day et al. |
| 7,869,474 | B2 | 1/2011 | Wysocki et al. |
| 7,894,057 | B2* | 2/2011 | Puzey ............ 356/326 |
| 7,903,704 | B2 | 3/2011 | Patel et al. |
| 8,018,981 | B2* | 9/2011 | Eckles et al. ............ 372/99 |
| 8,045,593 | B2 | 10/2011 | Gollier et al. |
| 8,149,407 | B1 | 4/2012 | Rao |
| 2001/0003482 | A1* | 6/2001 | Zare et al. ............ 356/432 |
| 2002/0071463 | A1* | 6/2002 | Garnache et al. ............ 372/45 |
| 2007/0014319 | A1 | 1/2007 | Hill et al. |
| 2011/0102788 | A1 | 5/2011 | Patel et al. |
| 2011/0216311 | A1 | 9/2011 | Kachanov et al. |
| 2012/0033220 | A1 | 2/2012 | Kotidis et al. |
| 2012/0206725 | A1 | 8/2012 | Vukovic-Cvijin et al. |
| 2013/0121353 | A1* | 5/2013 | Kub et al. ............ 372/11 |

OTHER PUBLICATIONS

Medhi et al., Infrared Intracavity Laser Absorption Spectrometer, Proc. Intl. Symp. Spectral Research (ISSSR), Jun. 2010, Springfield, MO.

SITIS Archives, Chemical/Bio Defense, 2008.

Medhi et al., Sensitivity of long-wave infrared intracavity laser absorption vapor detector, SPIE, 8236-55, V. 6, Jan. 3, 2012.

Mark A. Druy, Next-Generation Spectroscopic Technologies III, SPIE, vol. 7680, 248 pages, Apr. 2010.

G. Wysocki, Widely Tunable Mode-Hop Free External Cavity Quantum Cascade Laser for High Resolution Spectroscopic Applications, Applied Physics B: Lasers and Optics, 2005, vol. 81, p. 769-777, Houston, TX.

Gautam Medhi, Intracavity Laser Absorption Spectroscopy Using Mid-IR Quantum Cascade Laser, 2011, vol. 2, p. 1-7, FL.

Presentation at NASA Tech. Briefs Sensors Tech. Forum, Oct. 10, 2011.

* cited by examiner

90 ↘
Measure first spectrum in absence of test sample — 92
↓
Measure second spectrum in presence of test sample — 94
↓
Determine difference between first spectrum and second spectrum — 96
↓
Setting the distance as distance that yields the largest difference — 98
*FIG. 4*
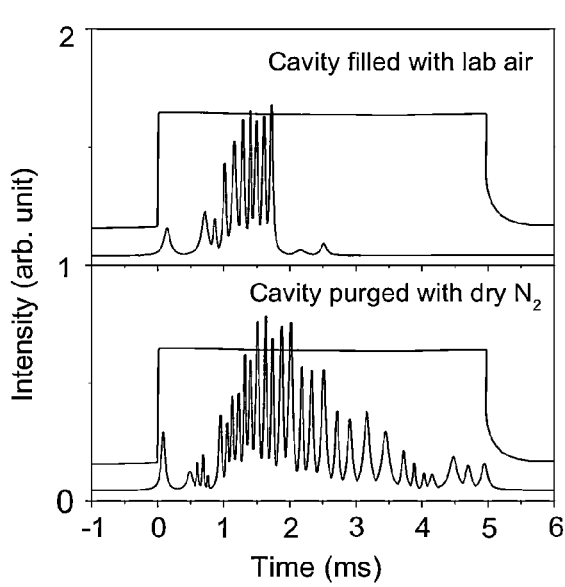
*FIG. 5a*
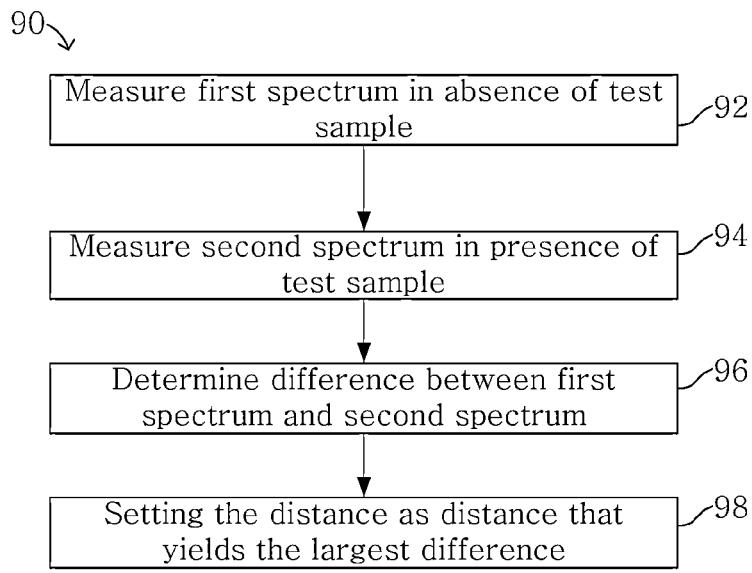
*FIG. 5b*

SYSTEM AND METHODS FOR MOLECULAR DETECTION USING INTRACAVITY LASER ABSORPTION SPECTROSCOPY

CROSS-REFERENCE TO RELATED APPLICATIONS

Priority is claimed to provisional application Ser. No. 61/630,157, filed Dec. 6, 2011 and titled "Vapor Sensor," and to provisional application Ser. No. 61/711,979, filed Oct. 10, 2012 and titled "System and Methods for Molecular Detection using Quantum Cascade Laser-Based Intracavity Laser Absorption Spectroscopy," which are incorporated by reference herein in their entireties.

STATEMENT REGARDING FEDERALLY SPONSORED RESEARCH OR DEVELOPMENT

This invention was made with at least partial government support under an SBIR grant awarded by the United States Army. The government has certain rights in the invention.

FIELD OF THE INVENTION

The invention relates to the field of intracavity laser absorption spectroscopy. More particularly, the invention relates to intracavity laser absorption infrared spectroscopy for detecting trace analytes.

BACKGROUND

It would be beneficial for different industries including those in the defense, law enforcement, environmental, food, medical, and materials fields to be able to detect trace amounts of gas-phase analytes using a reliable spectroscopic technique. Such a technique would allow them to detect contraband such as drugs, explosives, and/or contaminants on site. Unfortunately, however, very few spectroscopic techniques are sensitive enough to detect trace amounts of gas-phase analytes.

Intracavity laser absorption spectroscopy or "ICLAS" is one of the few spectroscopic techniques capable of doing so. In ICLAS, a test substance is introduced into the cavity of a laser that oscillates simultaneously across multiple resonator modes. If the test sample contains a substance that absorbs in the wavelength range emitted by the laser, the absorption features affect the laser spectrum by a measureable amount. ICLAS is very sensitive because it allows for extremely long effective path lengths and high spectral resolution.

Many molecules have a characteristic vibrational and/or rotational absorption spectrum in a particular band of the infrared wavelength region. This band, which ranges from wavelengths of about 3 $\mu$m to about 12 $\mu$m, is known as the "molecular fingerprint region" because the fundamental rotational/vibrational absorption bands for most molecules fall within these wavelengths. Because each molecule exhibits a unique absorption spectrum in the fingerprint region, it is often used to qualitatively identify molecules.

Quantum cascade lasers or "QCLs" are promising laser sources for performing ICLAS in the infrared wavelength region because they have broad gain spectra, a wide range of wavelengths, high output power, high duty cycle, and the ability operate at room temperature. The fingerprint region is easily accessible with QCLs. Combining a QCL with the ICLAS technique allows one to obtain the highest possible absorption cross-section because of the long path lengths and wavelengths that may be employed.

The inventor and his co-workers have already demonstrated that molecular detection using QCLs in an external cavity is possible. This previous work is described in the following references: (1) Medhi, et al. "Infrared Intracavity Laser Absorption Spectrometer," *Proc. Intl. Symp. Spectral Sensing Research (ISSSR)*, June 2010; (2) Medhi, et al., "Infrared Intracavity Laser Absorption Spectrometer," *Next Generation Spectroscopic Technologies III, Proceedings of SPIE*, Vol. 7680, Apr. 21, 2010; (3) Medhi, et al., "Sensitivity of long-wave infrared intracavity laser absorption vapor detector," *Laser Resonators, Microresonators, and Beam Control XIV*, Vol. 8236, Jan. 21, 2012; and (4) Medhi, et al., "Intracavity laser absorption spectroscopy using mid-IR quantum cascade laser," *Next Generation Spectroscopic Technologies IV, Proceedings of SPIE*, Vol. 8032, May 12, 2011. Each of these references is incorporated by reference herein in its entirety.

These references describe the development of a highly sensitive external cavity QCL-based ICLAS sensor by coupling an external cavity QCL with a Fabry-Perot interferometer. The Fabry-Perot interferometer included a pair of mirrors spaced apart to form a Fabry-Perot resonator. In order to record a spectrum, the spacing between the mirrors was adjusted so that the wavelength of the laser beam corresponded to a resonance mode of the Fabry-Perot resonator. This technique was shown to be very sensitive to trace gases but involves some serious drawbacks, which are discussed below.

SUMMARY

The inventor discovered that adjusting the spacing between the mirrors of the Fabry-Perot resonator introduced mechanical instabilities into the system and, because of these mechanical instabilities, the system's optical components had to be re-aligned over and over in order to maintain high sensitivity. This rendered the previous system very difficult to use for the detection of trace amounts of gas phase analytes. The invention described herein overcomes these drawbacks by minimizing the mechanical instabilities.

According to an embodiment of the invention, an improved method of detecting trace gases using an external cavity laser based ICLAS sensor minimizes mechanical instabilities by detecting the absorption of the analyte (a) without a Fabry-Perot resonator being necessary or (b) without the need to adjust the distance between the Fabry-Perot mirrors as the wavelengths of the laser are swept. This is accomplished by sweeping one or more of the QCL's gain parameters and recording the laser emission spectrum as a function of the laser gain parameter swept.

According to a first method aspect of the invention, a method of testing for gas-phase analytes that embodies these advantages involves generating a laser beam from a laser gain medium located within an external laser cavity and changing a gain parameter of the laser gain medium so that the laser gain medium emits across a range of wavelengths in response to the change. The laser beam is passed through a test sample positioned inside the external laser cavity as the gain parameter is changed. A change in the spatial or spectral mode distribution or dynamics of the laser emission spectrum is detected. It is then determined whether the change in the spatial or spectral mode distribution or dynamics of the laser emission spectrum is caused by the test sample.

According to a second method aspect of the invention, a gas-phase analyte testing method that embodies these advantages involves generating an infrared laser beam from a laser gain medium located within an external laser cavity having opposed reflective surfaces together defining an intracavity beam path that passes through the laser gain medium. While sweeping across plurality of infrared wavelengths by adjusting a gain parameter of the laser gain medium, a test sample intersecting the intracavity beam path is exposed to the laser beam. The laser beam exiting the external cavity is passed through a resonator having a pair of opposed reflectors that cause the laser beam to resonate therebetween. The spacing between the pair of opposed reflectors remains constant as the plurality of wavelengths are swept. The laser beam transmitted by the resonator is detected and it is determined whether an analyte is present in the test sample by characterizing an interaction between the laser beam and test sample.

According to a system aspect of the invention, a spectroscopy system that embodies these advantages includes an external laser cavity having opposed reflective surfaces together defining an intracavity beam path that passes through a laser gain medium positioned therein. The laser gain medium is capable of emitting infrared radiation across a range of wavelengths in response to a change in a gain parameter thereof. A sample cell for housing a sample is located inside the external laser cavity and in intracavity beam path. A resonator is in optical communication with an output of the external laser cavity. The resonator has a pair of opposed reflectors that cause the laser beam to resonate therebetween. A detector in optical communication with an output of the resonator is used to detect infrared radiation transmitted therefrom. A data acquisition unit in signal communication with the detector receives a signal characterizing an interaction between the infrared radiation and a sample in the sample cell, the signal resulting from the change in the gain parameter across the wavelengths emitted at a fixed separation between the opposed reflectors. The data acquisition unit determines, from the signal, whether an analyte is present in sample.

These and other aspects, embodiments, and features of the invention will be better understood in the context of the accompanying drawings and the following Detailed Description of Preferred Embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 is a flow diagram representing a method of optimizing the sensitivity of the molecular detection system, according to an embodiment of the invention.

FIG. 5a is a graph of the time dependence of the intensity of the laser beam transmitted by the Fabry-Perot resonator with its opposed reflective surfaces separated by a fixed distance. The top panel shows the laser excitation pulse and corresponding spectrum obtained while the external cavity was filled with ambient (lab) air. The bottom panel shows the laser excitation pulse and corresponding spectrum obtained while the external cavity was filled with dry nitrogen.

FIG. 5b is a graphical representation of the behavior observed in FIG. 5a. The wavelength band transmitted by the Fabry-Perot resonator (FP) is shaded. In the top panel, the QCL emission spectrum shifts towards longer wavelengths over time as temperature of the QCL medium changes during the pulse. The bottom panel shows that, when the external cavity is filled with dry nitrogen, the laser emission shifts toward shorter wavelengths where water vapor absorption occurs. This extends the time duration that the laser emission falls within the Fabry-Perot resonator's pass band.

DETAILED DESCRIPTION OF PREFERRED EMBODIMENTS

In the Summary above and in the Detailed Description of Preferred Embodiments, reference is made to particular features (including method steps) of the invention. Where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other features, ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

This invention may be embodied in many different forms and should not be construed as limited to the embodiments set forth herein. Rather, these embodiments are provided so that this disclosure will convey preferred embodiments of the invention to those skilled in the art.

Figure 1:
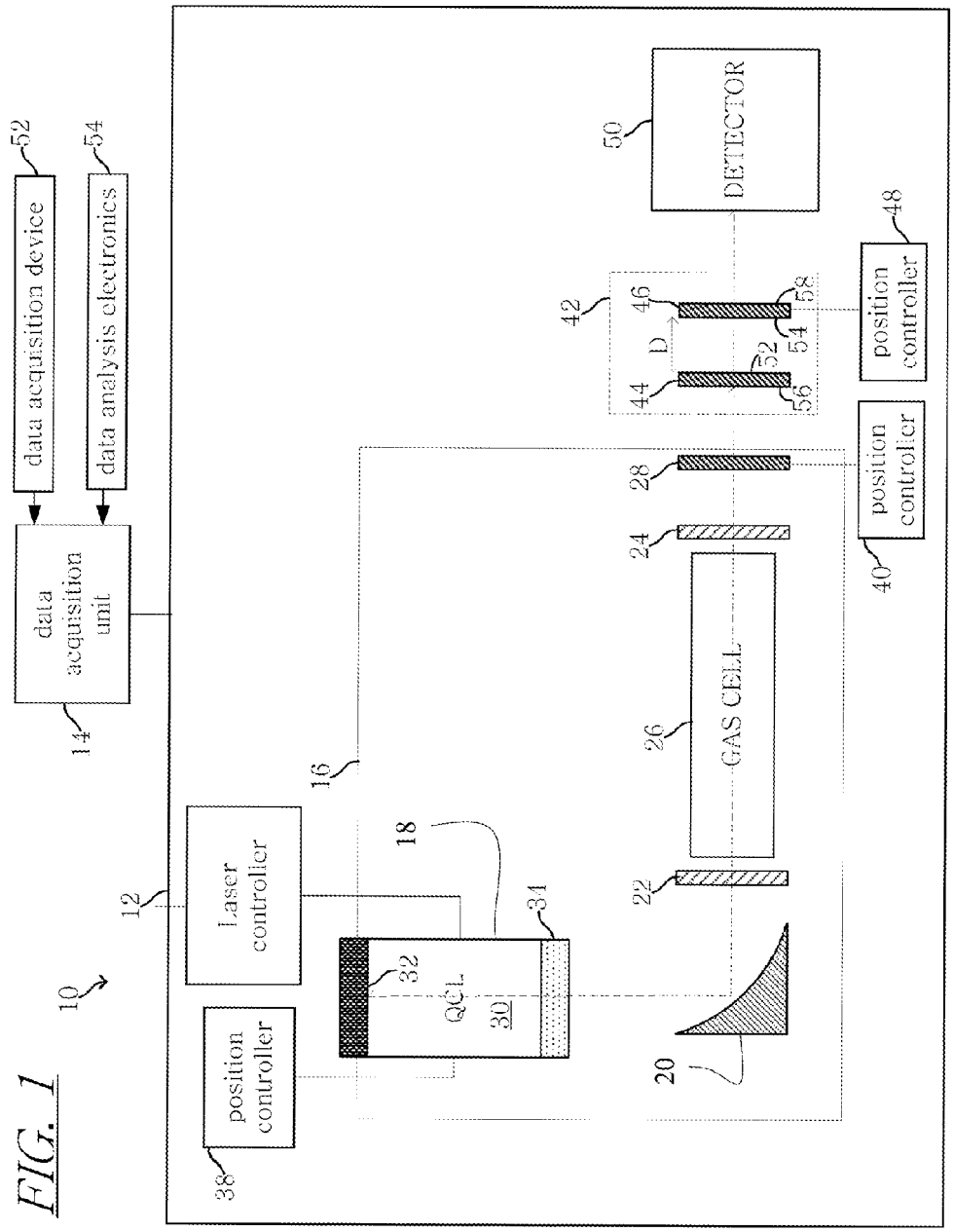
FIG. 1 is a schematic diagram of a molecular detection system, according to an embodiment of the invention.

A preferred system for gas-phase analyte testing, in accordance with an embodiment of the invention, is now described with reference to FIG. 1. The system 10 generally includes a spectrometer 12 in data communication with a data acquisition unit 14. As will be discussed in more detail later, the data acquisition unit 14 is equipped to analyze data it receives from the spectrometer 12 and translate that data into a signal indicative of the presence or absence of one or more analytes in the spectrometer 12.

The spectrometer 12 includes an external laser cavity 16 defined by a quantum cascade laser (QCL) 18, a parabolic mirror 20, a pair of optical diaphragms 22, 24 adjacent either end of a gas cell 26, and a semi-transparent reflector 28. The QCL 18 is equipped with a QCL laser medium 30 having a high reflectivity back facet 32 and a front facet 34 that is preferably coated with an antireflective coating material. When the QCL 18 is activated, it emits a laser beam that travels along a beam path, which is illustrated by the dotted lines ending with double arrows.

The beam exits the front facet 34 and is reflected by the off-axis parabolic mirror 20 through the first diaphragm 22, the gas cell 26, and the second diaphragm 24. The semi-transparent reflector 28 intercepts the beam and reflects most of it back in the opposite direction through the diaphragms 22, 24, the gas cell 26, against the parabolic mirror 20 and against the highly reflective back facet 32. Reflecting the beam back and forth between the back facet 32 and semi-transparent reflector 28 allow the beam to pass multiple times through the gas cell 26, which drastically increases the path length and, thereby, the sensitivity of the spectrometer 12. For some combinations of laser wavelength and analyte, an estimated path length for the spectrometer 12 is several hundred kilometers. This allows for the detection of weak absorbers in the gas cell 26 that have absorption coefficients well-below the usual threshold of FTIR spectrometers with long-path gas cells.

The relative positioning and orientation of the back facet 32 and the semi-transparent reflector 28 is preferably adjustable using at least one position controller mechanically linked to the QCL 18 and another position controller mechanically linked to the semi-transparent reflector 28. In the embodiment shown, a first position controller 38 controls the translational position and orientation of the QCL 18 while a second position controller 40 controls the translational position and orientation of the semi-transparent reflector 28. Accordingly, the position controllers 38, 40 allow the user to align the QCL's back facet 32 and semitransparent reflector 28 and to align the translational position of the QCL 18 in the focal plane of the off-axis parabolic mirror 20. By adjusting the relative translational spacing between the QCL 18 and semi-transparent reflector 28, the length of the external cavity 16 can be changed according to the user's preference. A preferred range of lengths for the external cavity 16 is between about 10 cm to about 50 cm. In order to facilitate optimal laser alignment, the positional controllers 38, 40 preferably also allow for angular alignment of the component(s) to which it (they) is (are) attached. In preferred embodiments of the system 10, the position controllers 38, 40 are high precision 3-axis optical mounts for angular and position alignment.

The portion of the laser beam that is not reflected back from the semi-transparent reflector 28 exits the external cavity 16 and enters a Fabry-Perot resonator 42 positioned along the beam path. The Fabry-Perot resonator 42 includes a pair of opposed semi-transparent reflectors 44, 46 that are spaced apart by a distance D that is sufficient to create resonance modes of the laser beam emitted from the QCL 18. Preferably, at least one of the semi-transparent reflectors 44, 46 of the Fabry-Perot resonator 42 is mechanically linked to an additional position controller 48, which functions similarly to those described above. This position controller 48, allows the distance D to be adjusted. When the distance D is adjusted, different modes resonate in the Fabry-Perot resonator 42. Preferably, the distance D is adjustable between about 200 µm to about 2 mm, depending on the spectral range of the QCL 18 and the desired spectral resolution. It is noteworthy, however, that this preferred range may be expanded according to the analyte to be detected and the QCL 18 used. In alternative embodiments, a Fabry-Perot etalon, which is a plate with two opposed reflective surfaces is employed.

A portion of the laser beam exits the Fabry-Perot resonator 42 and strikes a detector 50. The detector 50 detects radiation emitted from the semi-transparent reflector 28 for measuring the interaction of the test sample in the gas cell 26 with the intracavity beam. The detector 50 is adapted to convert the incident laser beam into an analog and/or digital signal that is fed to the data acquisition unit 14. There are various conventional infrared detectors that may be used to suit this purpose, including bolometers, photodiodes, and pyroelectric detectors. A preferred detector is a HgCdTe detector operating at about 77 Kelvin. In typical applications, however, it is desirable to use a detector 50 that is operable at room temperature. For these applications, an infrared pyroelectric detector may be more suitable.

The data acquisition unit 14 is in electrical communication with the detector 50 for generating the laser emission spectrum of the QCL 18 as a function of the emitted wavelength and for generating a waveform indicative of the time dependence of the signal from the detector 50. The data acquisition unit 14 also includes a data input channel for receiving the status of the laser gain parameter that is changed in order to sweep across the wavelength spectrum of the QCL 18.

The data acquisition unit 14 also includes a data acquisition device 52 such as an oscilloscope, an A/D converter, photon counter, and or a signal integrator. Data analysis electronics 54 in data communication with the data acquisition device 52 include one or more computer processors that determine values of various parameters of interest from signals characterizing the interaction of the test sample with the emitted beam. These parameters preferably include, but are not limited to: wavelength or frequency of the beam, absorption spectra, laser gain parameters, laser emission spectrum, time dependence of the laser emission spectrum, radiation intensity, and distance D between the Fabry-Perot resonator's 42 reflective surfaces 44, 46. In some embodiments, the data acquisition unit 14 functions are performed by a personal computer or the like. In alternative embodiments, the data acquisition unit 14 is contained within a housing that also houses the spectrometer 12, thereby making the system 10 compact and handheld.

With the forgoing general description of the system 10 in mind, additional details about preferred system components are now described.

The QCL laser medium 30 is preferably selected to emit at wavelengths that include the molecular fingerprint region of the infrared spectrum, or from about 3 µm to about 20 µm. The QCL laser medium 30 is semi-conductor based and is capable of operating in a multi-mode regime, meaning that it can emit across a range of wavelengths distributed about an average wavelength at one time.

The wavelength of the emitted beam can be adjusted by varying one or more of the QCL's gain parameters, such as the voltage or current supplied to operate the laser or the temperature of the QCL medium 30. As previously mentioned, and will be described in more detail later, the inventor found that sweeping the emitted wavelengths of the QCL 18 by varying one or more of the laser gain parameters allows for the distance D to be fixed while the test sample spectrum is recorded, thereby eliminating the mechanical instabilities associated with varying the distance D while the spectrum is recorded. The multimode spectrum of the QCL 18 beam is tuned across the emission range of the QCL by changing one or more of its gain parameters. Due to competition of modes in the multimode laser emission spectrum, this method works even in situations when the test sample does not absorb at a specific resonant wavelength corresponding to the distance D between the reflectors 44, 46. Moreover due to mode competition the change of the signal passed through the resonator 42, while sweeping one of the laser gain parameters reflects information about unique absorption spectrum of the test sample.

The QCL medium 30 is preferably operable in continuous wave and/or pulse mode. When the laser gain parameter that is varied is the temperature of the QCL 18 medium, it may be advantageous to use pulses that are at least as long as or longer than the time it takes for the temperature fluctuations caused by the initial onset of the pulse to relax, which will typically depend on the QCL 18 that is used.

The diaphragms 22, 24 are preferably adjustable optical diaphragms for controlling the transverse modes of the fine laser mode spectrum. They are not necessary in all embodiments of the invention.

The highly reflective coating on the back facet 32 of the QCL medium 30 can be made from any conventional coatings known to reflect infrared radiation. The anti-reflective coating on the laser output facet 34 of the QCL medium 30 is adapted to prevent the beam from being reflected from the front side of the QCL medium 30. The anti-reflective coating can be made from any conventional coating known to prevent infrared radiation from being reflected.

Figure 2:
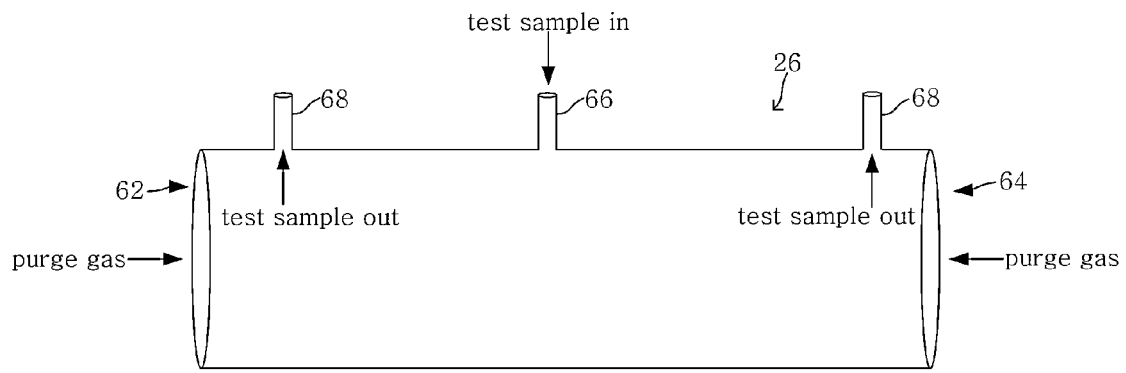
FIG. 2 is a schematic diagram of a preferred example of a gas cell useful in the molecular detection system.

The gas cell 26 is adapted to hold a test sample in the beam path so that the beam will pass through the test sample for determining whether the test sample contains an analyte. The shape of the gas cell 26 shown in FIG. 1 is for illustrative purposes only. A more detailed embodiment of the gas cell 26 is shown in FIG. 2. In the embodiment shown in FIG. 2, the gas cell 26 is formed from a hollow tube having a pair of open terminal ends 62, 64, a test sample input port 66, and a pair test sample output ports 68. In practice, the test sample is introduced into the gas cell 26 by pumping it through the test sample input port 66 and is removed from the gas cell 26 by allowing it to exit the test sample output ports 68. Inert purge gas is allowed to flow into the gas cell 26 via the open terminal ends 62, 64. By maintaining positive pressure on the gas cell 26 using the purge gas, the test sample is inhibited from exiting the gas cell via the open terminal ends 62, 64.

Referring back now to FIG. 1, the off-axis parabolic mirror 20 is used to couple the QCL 18 with the external laser cavity's 16 semi-transparent reflective surface 28. The position and orientation of the QCL 18 is aligned in the focus of the mirror 20 using position controller 38. Although the focal length and composition of the parabolic mirror 20 is not a critical feature, the inventor obtained good results with a gold coated parabolic mirror having a focal length of 25.4 mm.

In principle, using the parabolic mirror 20 is not necessary since there are alternative techniques that can also be used. For example, a collimating lens can be used in place of the parabolic mirror 20 or the laser can be aligned with a single spherical mirror to form a semi-confocal resonator. Regardless, it is preferred that the laser beam emitted from the QCL 18 pass through an open region to which the analyte vapor has access and that a portion of the beam be collected and refocused back into the QCL medium 30.

The semi-transparent reflector 28 is adapted to reflect a portion of the beam while also allowing another portion of the beam to pass therethrough. In a preferred embodiment, this is achieved using a highly reflective gold mirror with a millimeter sized out-coupling hole passing therethrough in a position that is along the beam path. A preferred size of the out-coupling hole is about 1 mm. Although using the out-coupling hole is preferred, there are other types of semi-transparent reflectors that can be used. For example, a partially transparent mirror without an out-coupling hole can be substituted. Scattered radiation can even be used if desired.

The Fabry-Perot resonator's 42 pair of semi-transparent reflectors 44, 46 are preferably made of ZnSe panels having 2 mm thickness. The facing surfaces 52, 54 are coated with a highly reflective coating. In a preferred embodiment, the highly reflective coating reflects about 97.5% of the incident infrared radiation. The outer surfaces 56, 58 are preferably coated with an anti-reflective coating.

The semi-transparent reflectors 44, 46 of the Fabry-Perot resonator 42 may be positioned to eliminate undesired secondary resonances within the panels themselves. In a preferred embodiment, the semi-transparent reflectors 44, 46 are wedged about 30 arcmin to do so.

As discussed above, the molecular detection technique discovered by the inventor allows for the distance D between the Fabry-Perot resonator's 42 semi-transparent reflectors 44, 46 to remain fixed while the test sample's absorbance is recorded. This is a significant departure from previously disclosed methods of molecular detection using QCL-based external cavity ICLAS spectroscopy, in which the distance between the Fabry-Perot resonator's 42 semi-transparent reflectors 44, 46 was adjusted as the spectrum was recorded. This introduced a severe technical drawback, namely, the mechanical instabilities associated with adjusting the distance between the semi-transparent reflectors 44, 46 made the previous system tedious and time-consuming to use since the alignment of all of the optical components must be adjusted over and over to maintain high sensitivity.

The inventor has overcome this drawback by keeping the distance D fixed while the test sample spectrum is recorded. In order to accomplish this, the wavelengths emitted by the QCL 18 are swept across the emission spectral range of the QCL 18 by changing one or more of the laser gain parameters using a laser controller 60. The laser controller 60 is a conventional laser controller that includes laser current, laser voltage, and temperature control and monitoring components. The laser controller 60 is used to tune the QCL 18 thermally and electronically. The laser controller 60 also includes electronic circuitry adapted to control and monitor one or more of the QCL's gain parameters, including but not limited to: temperature, current, and voltage.

In a preferred embodiment, the gain parameter that is varied is the temperature of the QCL 18. When the QCL medium 30 is activated, it heats slowly, which causes the wavelength of the emitted beam to shift from one wavelength to another. As the emitted wavelength shifts across the QCL's 18 emission spectrum, the intensity transmitted by the Fabry-Perot resonator 42 also changes. The Fabry-Perot resonator's 42 transmitted intensity can be monitored in real time using the data analysis electronics 54 in communication with the data acquisition system 14. Monitoring the Fabry-Perot resonator's 42 transmitted intensity as the QCL 18 sweeps through its emission spectrum allows for the changes of the QCL's emission spectrum to be detected without changing the distance D between the Fabry-Perot resonator's 42 semi-transparent reflectors 44, 46.

When the gain parameter that is swept is the temperature of the QCL medium 32, it is preferred that laser pulses of at least 1 ms are employed. This is because the QCL emission spectrum tends to be unstable prior to the 1 ms time point in the pulse due to rapid temperature changes in the QCL medium 32. After 1 ms, the emission spectrum stabilizes, but continues a slow adiabatic drift due to the slower heating of the QCL medium 30. The shift in the emission spectrum is repeatable from pulse to pulse. It is to be understood, however, that the length of the laser pulse may vary depending on the QCL 18 employed. Accordingly, the preferred length of the laser pulse may be less than 1 ms in some embodiments.

In alternative embodiments of the system, with or without the Fabry-Perot resonator 42 to analyze the laser emission spectrum, the system detects changes in the spatial mode distribution as the wavelengths are swept. This is achieved by incorporating a detector that functions as an infrared camera, having a pair of x and y spatial axes. Alternatively, the system detects changes in the mode dynamics as the wavelengths are swept by observing the time-dependence of the impedance of the QCL 18. This is achieved by detecting spikes in the QCL's 18 impedance, which are associated with laser mode hopping events that occur during the sweep. The spikes are detected by monitoring the change in the ratio of the voltage drop on the QCL medium 30 and the current on the QCL medium 30. These alternative embodiments allow for additional analysis of the fine mode structure of the laser, which may not be resolved by Fabry-Perot resonator 42, thus enhancing overall sensitivity of the system to the presence of analytes.

Methods of detecting gas-phase analytes are now described with reference to FIGS. 3 and 4. These methods may be performed using the system 10 just described or an alternative system capable of performing the method steps or their equivalents. The methods steps are described in connection with the system 10, solely to help the reader understand their functionality.

Figure 3:
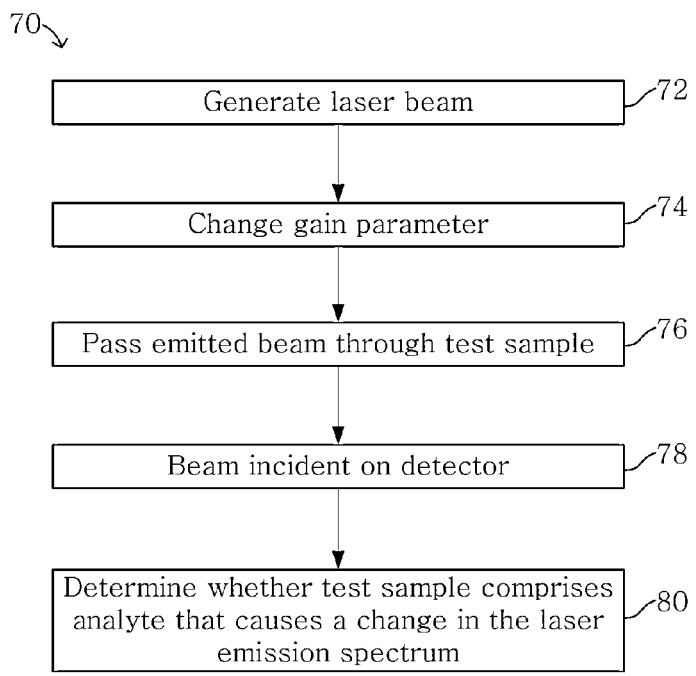
FIG. 3 is a flow diagram representing a method of detecting one or more gas-phase analytes, according to an embodiment of the invention.

Referring to FIG. 3, a preferred method of detecting a gas-phase analyte 70, in accordance with an embodiment of the invention includes the steps shown. At block 72, a laser beam is generated from an external cavity laser source having an emission spectrum that is dependent upon one or more laser gain parameters such as temperature, voltage, and current. The preferred laser source is capable of emitting infrared radiation in at least a portion of the molecular fingerprint region. For the reasons discussed above, a QCL is particularly preferred.

At block 74, the emission band of the laser source is swept from a first wavelength to a second wavelength by adjusting one or more of the laser source's gain parameters. The laser beam passes through a gas-phase test sample located within a laser cavity (block 76), such as the external cavity 16 of the system 10. The laser beam makes multiple passes through the test sample by reflecting back and forth between a set of reflectors on opposed ends of the laser cavity. It should be understood that the test sample is present within the external cavity when the laser beam is generated. Because of this, the laser emission spectrum will depend, not only on the laser gain medium, but also the identity of the test sample. Accordingly, in most embodiments, the actions that take place during blocks 72-76 occur at substantially the same time.

The laser beam is subsequently directed from the laser cavity to a resonator (block 76), such as the Fabry-Perot resonator 42, having a pair of opposed reflective surfaces for generating resonance modes of the laser beam therebetween.

A portion of the laser beam exits the resonator and becomes incident upon a detector (block 78) capable of detecting infrared radiation within the wavelengths swept.

At block 80, a data acquisition unit in data communication with the detector, receives and analyzes the data from the detector and determines whether the test sample contains one or more analytes that have absorbance bands within the wavelengths swept. The absorption bands cause changes to the detected laser gain spectrum.

Advantageously, this method is performed while the distance between the reflectors of the resonator remains substantially constant. Detecting the effect of absorption bands on the laser spectrum while keeping the distance between the reflectors of the resonator substantially constant is possible due to competition between the laser modes. Remarkably, even if the emitted wavelength does not correspond to the location of an absorption band, the absorption band is still detected due to its effect on the net laser gain spectrum.

Adjusting one or more of the laser gain parameters causes a dynamic change of the laser beam's intensity at a given wavelength. When the emitted wavelengths pass through an absorption band of an analyte, the analyte's absorption changes the detected intensity of the beam. This change is unique to the analyte in the test sample.

When the laser gain parameter that changes is the QCL medium temperature, the natural temperature drift of the QCL medium in the quasi-CW regime is preferably used. The exact parameters will be a function of the particular QCL medium. The inventor has achieved good results using long ~10 ms pulses with ~10% duty cycle. Temperature sweeping causes laser mode hopping events, which in turn are extremely sensitive to the presence of an analyte vapor with a wavelength dependent absorption spectrum inside the gas cell. The discrete absorption bands of the analyte changes the laser mode-hopping dynamics at emission wavelengths in the vicinity of the absorption band. This can be monitored by a detection system with a narrow spectral window, such as, for example, the Fabry-Perot resonator and detector combination described above. Because the analyte detection algorithm is based on such mode hopping events, the sensitivity of the system is largely independent of the dynamic resolution and signal to noise ratio of the detector.

If desired, the distance between the resonator's pair of reflectors is pre-determined by following the method illustrated in FIG. 4. Referring to FIG. 4, a method 90 of optimizing the sensitivity of the system is now described. At block 92, a first spectrum is measured in the absence of the test sample by simultaneously adjusting the distance between the resonator's pair of opposed reflectors and changing the gain parameter. At block 94, a second spectrum is measured in the presence of the test sample by simultaneously adjusting the distance between the resonator's pair of opposed reflectors and changing the gain parameter. The two spectra are recorded by the data acquisition unit. At block 96, the data analysis electronics determine the difference between the first spectrum and second spectrum. At block 98, the distance between the resonator's pair of opposed reflectors is set as the distance that yielded the largest difference.

EXAMPLES

The embodiments of the invention described above will be even better understood in the context of the following examples. These examples are provided for illustration purposes and are not intended to limit the scope of the invention in any way.

Example 1

Time Dependence of the Intensity Transmitted from a Fabry-Perot Resonator with Reflectors Separated by a Fixed Distance This example shows how the intensity transmitted by the Fabry-Perot resonator changes over time as the temperature laser gain parameter of the QCL medium is swept. For these experiments a QCL commercially available from Maxion Technologies, Inc. (College Park, Md.) was used. The distance between the Fabry-Perot resonator's reflectors remained fixed during the measurements. The QCL was excited slightly above the threshold current with 5 ms pulse duration at 20% duty cycle. The excitation current profile in the active chip during the pulse is also shown in both plots of FIG. 5a.

FIG. 5a presents oscilloscope traces of the laser emission intensity after the beam was transmitted through the narrow fixed pass band of the Fabry-Perot resonator. The laser emission spectrum shifted in time toward longer wavelengths (lower frequencies) as the QCL temperature increased. In the upper plot ~12 laser spectral peaks were observed passing through the transmission window of the resonator between 0 (beginning of the laser pulse) and 2.5 ms. After 2.5 ms, laser emission no longer occurred at wavelengths within the resonator's pass band.

The lower plot of FIG. 5a reveals the effect of purging the external cavity with dry nitrogen. This results in the appearance of several additional spectral peaks passing through the Fabry-Perot's transmission window after 2.5 ms, where the laser emission was previously blocked by the resonator. When ambient air was reintroduced into the external cavity, the trace recorded in the upper plot was restored.

Although not intending to be bound by theory, FIG. 5b illustrates a plausible explanation for the effect recorded in FIG. 5a. The QCL emission spectrum shifted towards longer wavelengths with time as the QCL temperature rose. Only that portion of the spectrum within the resonator's pass band (shaded box) reached the detector. Purging the laser cavity shifted the laser emission toward shorter wavelengths. Subsequently, this extends the duration that laser emission remains within the FP bandpass.

Example 2

Detection of Trace Vapors of an Analyte

This example illustrates how the system and method were used to detect trace vapors of an analyte.

The procedure used in this example was as follows. First, the reference laser emission intensity was measured as a function of time during a single laser pulse at chosen system operating parameters. These parameters include background QCL temperature, current, pulse duration, repetition rate, and initial Fabry-Perot resonator reflector separation. The measurement was repeated for different Fabry-Perot separations, resulting in a time-resolved spectrum without the presence of analyte vapor inside the external cavity. An example of such a reference spectrum is presented in FIG. 6a (left).

Figures 6A, 6B:
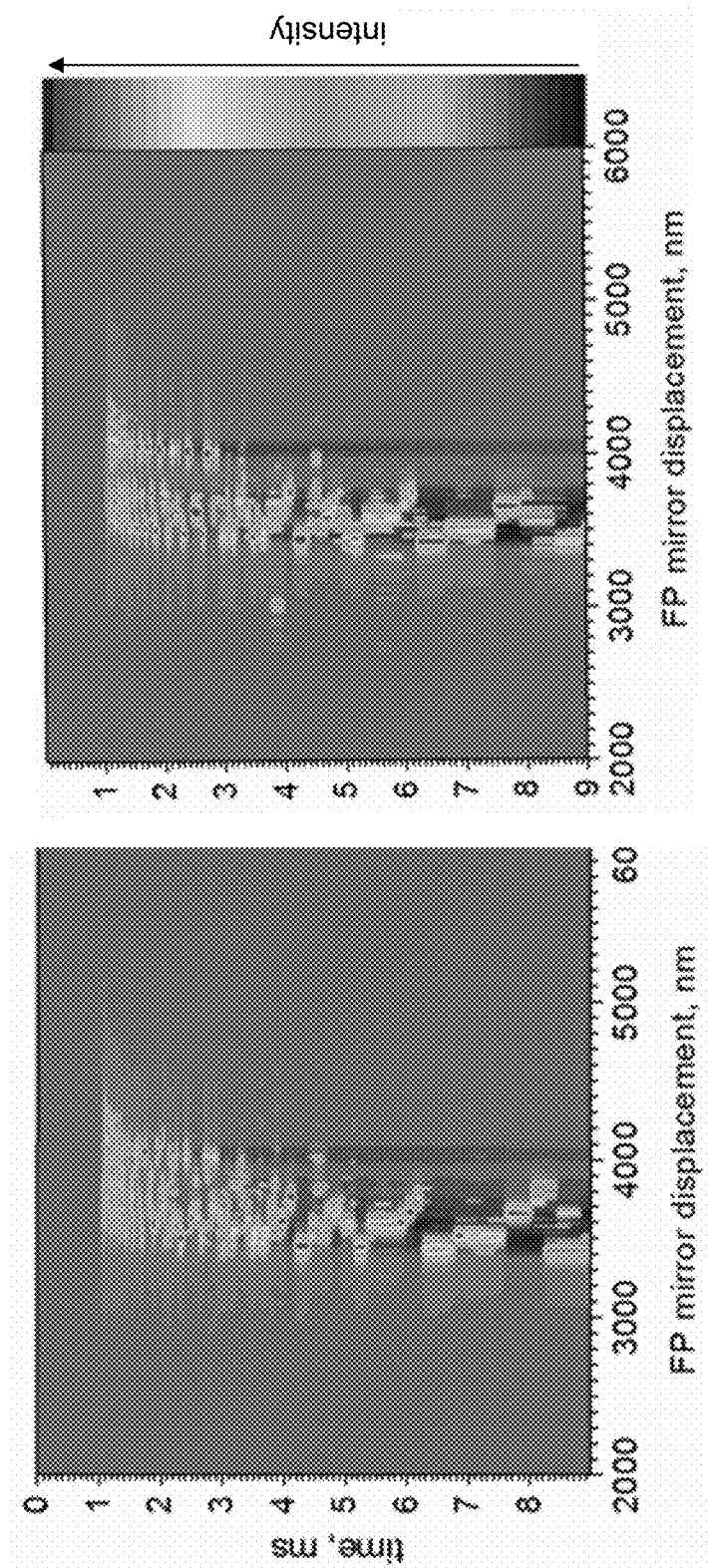
FIG. 6a is a graph showing the time dependence of the laser gain spectrum during a pulse recorded at different displacements of the Fabry-Perot resonator's reflective surfaces (FP mirror displacement) without a test sample in the external cavity. The z-axis is the spectrum intensity, which is represented by a color scale.
FIG. 6b is a graph showing the time dependence of the laser gain spectrum during a pulse recorded at different displacements of the Fabry-Perot resonator's reflective surfaces (FP mirror displacement) with a test sample in the external cavity. The z-axis is the spectrum intensity, which is represented by a color scale.

To record the reference spectrum shown in FIG. 6a, a laser pulse was applied at a series of separation distances between the Fabry-Perot resonator's reflectors. The time scale of the laser pulse is shown on the y-axis as time in units of milliseconds (ms) and the distance is shown along the x-axis as mirror displacement in nanometers (nm). The pulse began at about 1 ms and continued to about 9 ms. The z-axis, which is shown in terms of color coded intensity, represents the spectrum recorded at each mirror displacement. The total displacement corresponded to one half wavelength of the 8 μm laser emission spectrum. The laser emission spectrum shifted towards smaller displacement, or shorter wavelength, as the QCL medium heated during the pulse.

Next, the same measurement was performed when ammonia vapor was present in the gas cell. The laser operation parameters and procedure were substantially identical to those used to record the reference spectrum.

FIG. 6b shows the spectrum in the presence of ammonia vapor. An absorption line appeared at about 3900 nm mirror displacement, the evidence for which is the loss of spectral intensity at this position. The identity of the molecule responsible for this absorption is still uncertain. It could be ammonia or water vapor. Additionally, a pronounced anomaly appeared in the spectrum at about 3050 nm, which in principle can be also be used for the chemical recognition.

Figure 7:
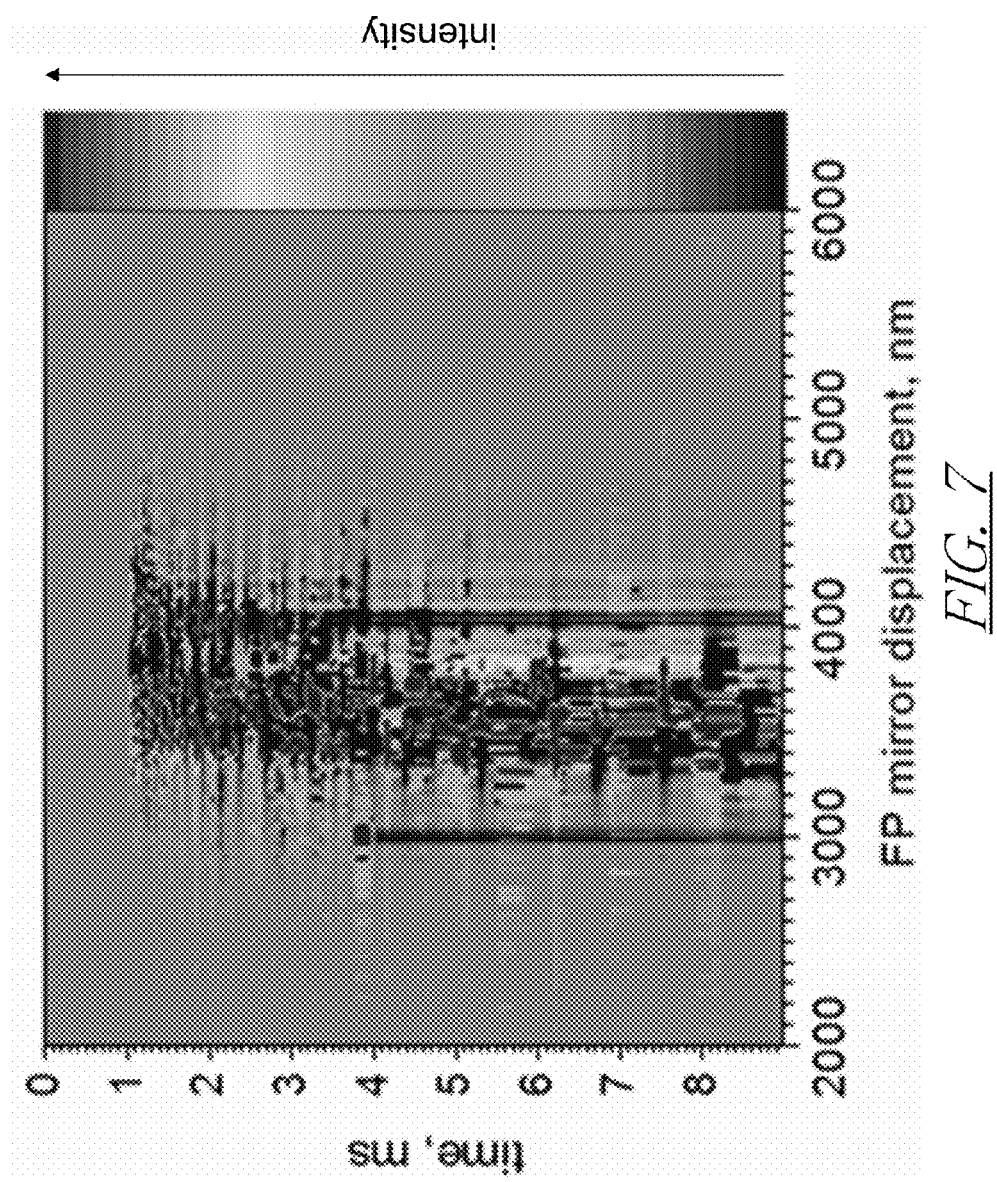
FIG. 7 is a graph showing the difference between the spectrum of FIG. 6a and the spectrum of FIG. 6b.

The difference between the two spectra was calculated using the data acquisition electronics. This is presented in FIG. 7. This differential spectrum enhances the effect of the analyte's absorbance, making it more visible.

These data allowed for the selection of the mirror displacement (or distance D) that provided the strongest change of the laser mode hopping pattern. For this particular example, this occurred at about 3000-3100 nm. Choosing this position gives a single temporal slice of the spectrum, as shown in FIG. 8.

Figure 8:
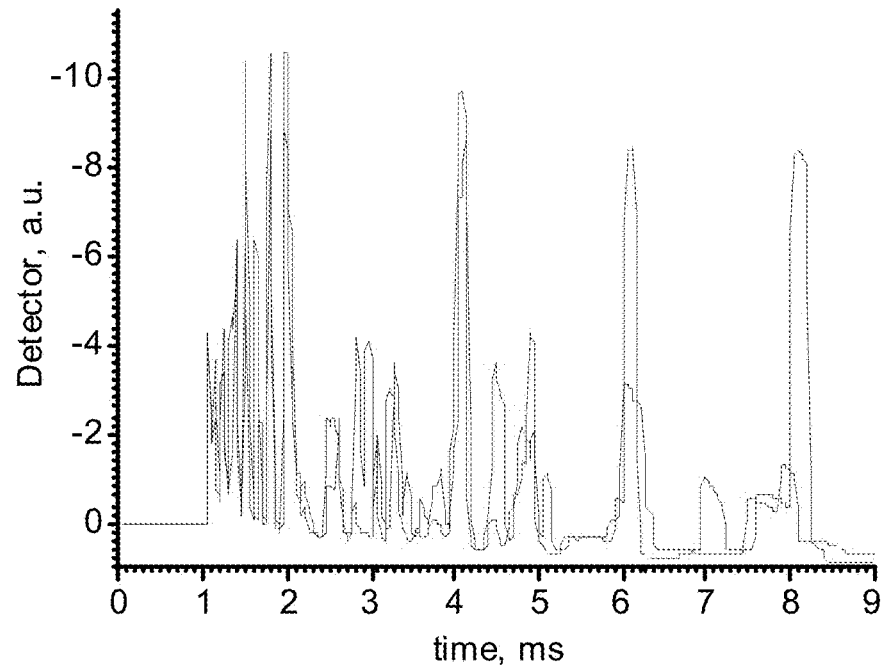
FIG. 8 is a graph of the emission waveform at FP mirror displacement 3740 nm without (blue) and with (red) ammonia vapor in the external cavity.

FIG. 8 shows the emission waveforms at D=3740 nm without (blue) and with (red) ammonia vapor in the gas cell.

Figure 9:
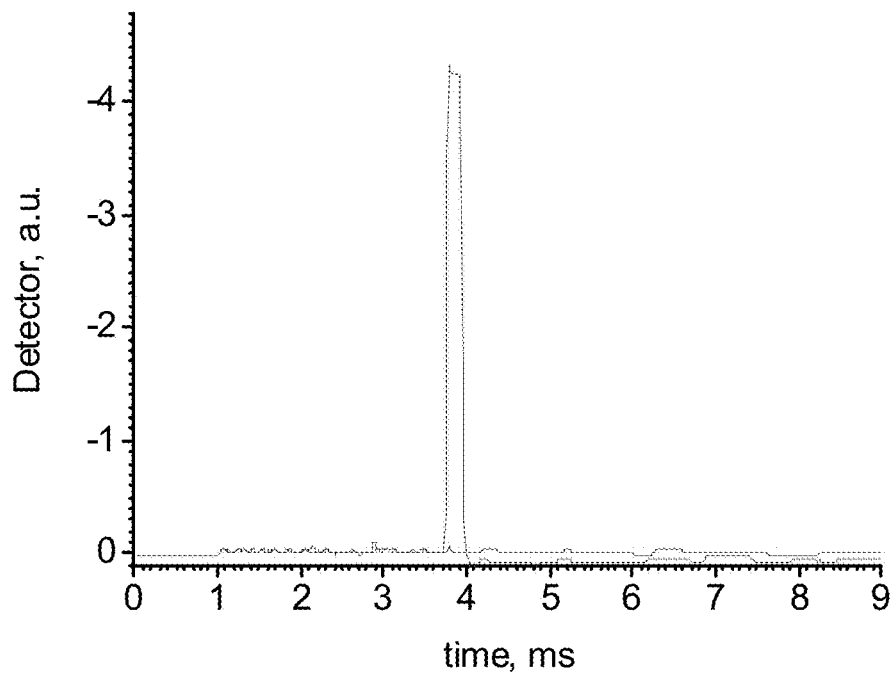
FIG. 9 is a graph of the emission waveform at FP mirror displacement 3020 nm without (blue) and with (red) ammonia vapor in the cavity. This position provides the best signal to noise ratio.

FIG. 9 shows emission waveforms at D=3020 nm without (blue) and with (red) ammonia vapor in the gas cell. This distance position provides the best signal to noise ratio and is optimal for detection of ultra-low trace vapor concentrations.

Example 3

Spatial Detection of the QCL Beam Modes

Figure 10:
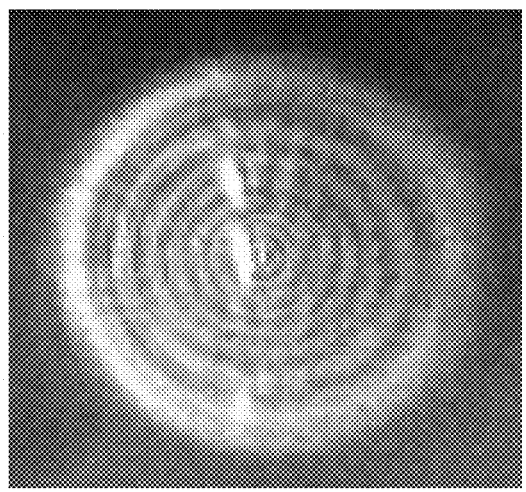
FIG. 10 is an IR camera image of the laser beam's spatial profile obtained for a first transverse mode structure.
Figure 11:
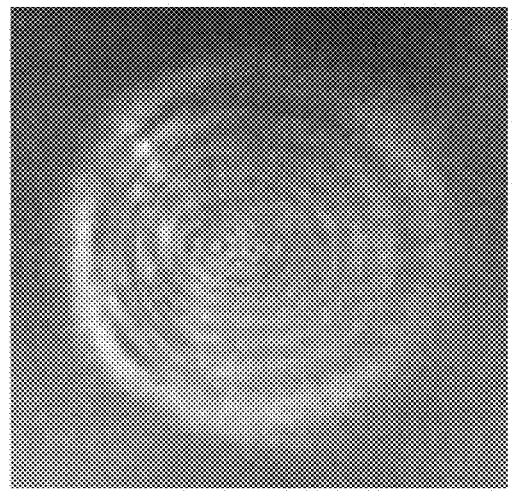
FIG. 11 is an IR camera image of the laser beam's spatial profile obtained for a second transverse mode structure.

This example shows that the spatial distribution of the QCL beam can be detected using an IR camera as the detector. FIGS. 10 and 11 show two different spatial mode distributions for different transverse mode structures.

We expect similar changes of the laser transverse mode structure, in response to the presence of an absorbing analyte inside the external laser cavity.

Example 4

Detection of Spectral Mode Dynamics

Figure 12:
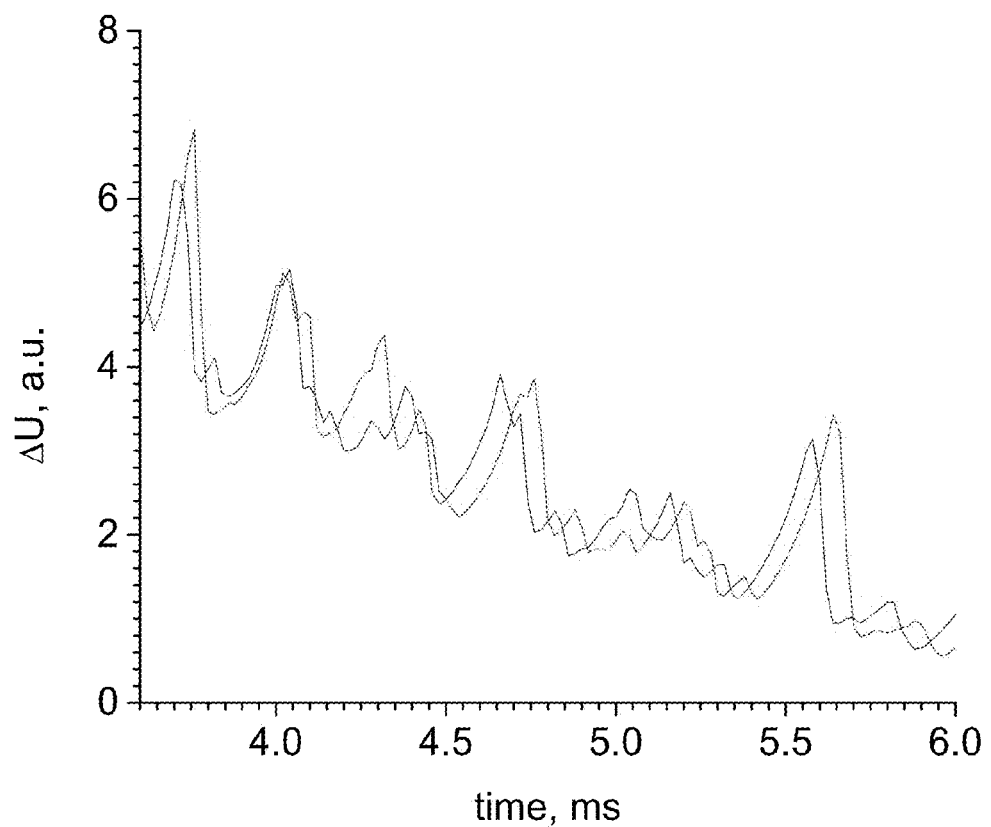
FIG. 12 is a graph showing fragments of the QCL voltage waveforms for dry nitrogen inside the laser cavity (blue) and nitrogen with $H_2O$ vapor (~50% humidity level) (red). The laser wavelength was 8.0 μm, the operation current was =900 mA, and the temperature was 15° C.
Figure 13:
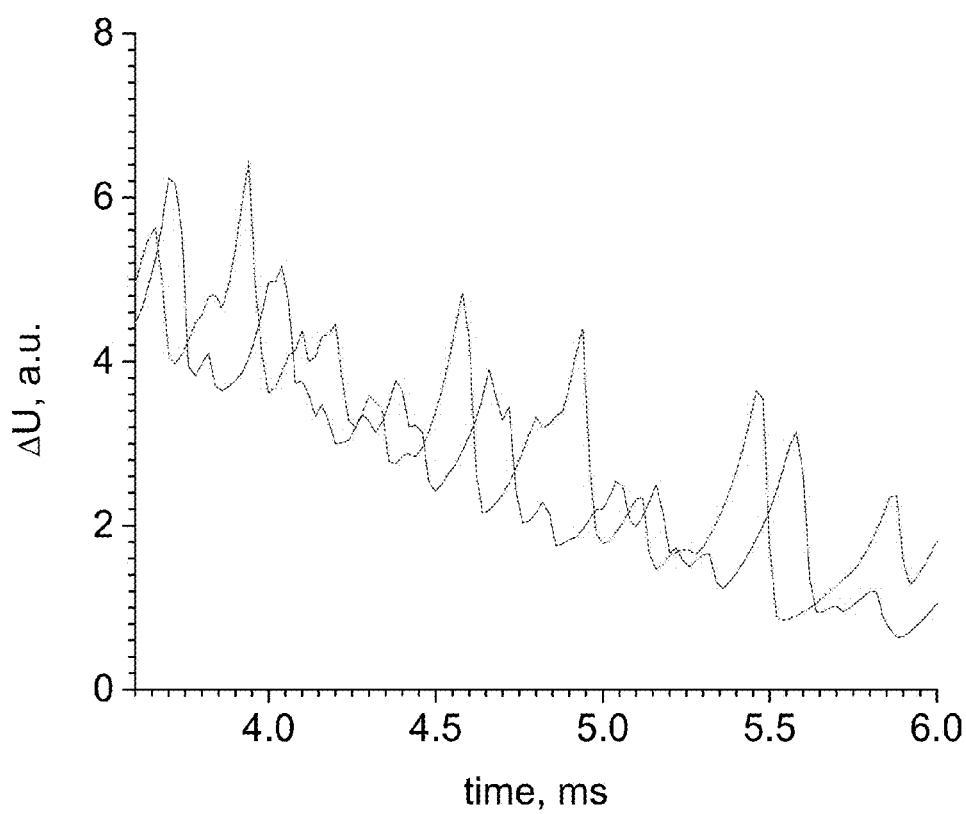
FIG. 13 is a graph showing fragments of the QCL voltage waveforms for dry nitrogen inside the laser cavity (blue) and laboratory air (red). The laser wavelength was 8.0 μm, the operation current was =900 mA, and the temperature was 15° C.

This example shows the actual change of the voltage waveform, measured across the QCL electrical terminals over time, in response to different analytes. With reference to FIGS. 12 and 13, the fact that the voltage spikes are shifting in different directions demonstrates different absorption spectra of wet nitrogen and laboratory air. Accordingly, the system is able to distinguish an analyte present in the laboratory air sample aside from the humidity.

The invention has been described above with reference to the accompanying drawings, in which preferred embodiments of the invention are shown. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. The skilled should understand that the methods and materials used and described are examples and may not be the only ones suitable for use in the invention.

In the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and as defined in the appended claims.

That which is claimed is:

1. A method of testing for gas-phase analytes, the method comprising:
    (a) generating a laser beam from a laser gain medium located within an external laser cavity;
    (b) changing a gain parameter of the laser gain medium so that the laser gain medium emits across a range of wavelengths in response to the change;
    (c) passing the laser beam through a test sample as the gain parameter is changed, the test sample being located inside the external laser cavity;
    (d) detecting a change in the spatial or spectral mode distribution or dynamics of the laser emission spectrum by passing the laser beam exiting the external cavity through a Fabry-Perot resonator having a pair of parallel opposed reflectors spaced apart by a fixed distance as the gain parameter is changed; and
    (e) determining whether the change in the spatial or spectral mode distribution or dynamics of the laser emission spectrum is caused by the test sample;
    (f) wherein the fixed distance is predetermined by:
        measuring a first spectrum in the absence of the test sample by simultaneously changing the gain parameter and the distance between the reflectors;
        measuring a second spectrum in the presence of the test sample by simultaneously changing the gain parameter and the distance between the reflectors; and
        determining the difference between the first spectrum and second spectrum; and
        setting the distance between the reflectors as the distance that yielded the largest difference between the first spectrum and second spectrum.

2. The method of claim 1, wherein the gain parameter changed is the temperature of the laser gain medium.

3. The method of claim 1, wherein the gain parameter changed is selected from the group consisting of voltage supplied to the laser gain medium, current supplied to the laser gain medium, and a combination thereof.

4. The method of claim 1, wherein the laser gain medium is a quantum cascade laser.

5. The method of claim 1, wherein detecting a change in the spatial or spectral mode distribution or dynamics of the laser emission spectrum comprises detecting a change in the spatial mode intensity distribution by directing the laser beam exiting the external cavity onto an infrared camera.

6. The method of claim 1, wherein detecting a change in the spatial or spectral mode distribution or dynamics of the laser emission spectrum comprises detecting a change in the impedance of the laser gain medium during a pulse of laser beam.

7. A gas-phase analyte testing method comprising:
    (a) generating an infrared laser beam from a quantum cascade laser located within an external laser cavity having opposed reflective surfaces together defining an intracavity beam path that passes through the quantum cascade laser;
    (b) exposing a test sample intersecting the intracavity beam path to the laser beam while sweeping across plurality of infrared wavelengths by adjusting a gain parameter of the quantum cascade laser;
    (c) passing the laser beam exiting the external cavity through a resonator having a pair of opposed reflectors that cause the laser beam to resonate therebetween, while maintaining constant spacing between the pair of opposed reflectors as the plurality of wavelengths are swept;
    (d) detecting the laser beam transmitted by the resonator; and
    (e) determining whether an analyte is present in the test sample by characterizing an interaction between the laser beam and test sample
    (f) wherein the constant spacing between the reflective surfaces is pre-determined by:
        measuring a first spectrum in the absence of the test sample by simultaneously changing the gain parameter and the distance between the reflectors;
        measuring a second spectrum in the presence of the test sample by simultaneously changing the gain parameter and the distance between the reflectors; and
        determining the difference between the first spectrum and second spectrum; and setting the distance between the reflectors as the distance that yielded the largest difference between the first spectrum and second spectrum.

8. The method of claim 7, wherein the gain parameter changed is the temperature of the laser gain medium.

9. The method of claim 7, wherein the gain parameter changed is selected from the group consisting of voltage supplied to the laser gain medium, current supplied to the laser gain medium, and a combination thereof.

10. The method of claim 7, wherein detecting the laser beam transmitted by the resonator comprises detecting a change in the spatial mode intensity distribution by directing the laser beam exiting the resonator onto an infrared camera.

11. A spectroscopy system comprising:
    (a) an external laser cavity having opposed reflective surfaces, maintained at a constant spacing therebetween, together defining an intracavity beam path that passes through a laser gain medium positioned therein, the laser gain medium being capable of emitting infrared radiation across a range of wavelengths in response to a change in a gain parameter thereof;
    (b) a sample cell for housing a sample inside the external laser cavity and in intracavity beam path;
    (c) a resonator in optical communication with an output of the external laser cavity, the resonator having a pair of opposed reflectors that cause the laser beam to resonate therebetween;
    (d) a detector in optical communication with an output of the resonator for detecting infrared radiation transmitted therefrom; and
    (e) a data acquisition unit in signal communication with the detector for receiving a signal characterizing an interaction between the infrared radiation and a sample in the sample cell, the signal resulting from the change in the gain parameter across the wavelengths emitted at a fixed separation between the opposed reflectors, and determining, from the signal, whether an analyte is present in sample (f) wherein the constant spacing between the reflective surfaces is pre-determined by:
  measuring a first spectrum in the absence of the test sample by simultaneously changing the gain parameter and the distance between the reflectors;
  measuring a second spectrum in the presence of the test sample by simultaneously changing the gain parameter and the distance between the reflectors; and
  determining the difference between the first spectrum and second spectrum; and setting the distance between the reflectors as the distance that yielded the largest difference between the first spectrum and second spectrum.

12. The spectroscopy system of claim 11, wherein the gain parameter is the temperature of the laser gain medium.

13. The spectroscopy system of claim 11, wherein the gain parameter is selected from the group consisting of voltage supplied to the laser gain medium, current supplied to the laser gain medium, and a combination thereof.

14. The spectroscopy system of claim 11, wherein the laser gain medium is a quantum cascade laser.

\* \* \* \* \*